United States Patent
O'Carroll et al.

(10) Patent No.: US 10,525,256 B2
(45) Date of Patent: Jan. 7, 2020

(54) INTERVENTIONAL MEDICAL SYSTEMS, CATHETERS, AND METHODS

(71) Applicant: Medtronic, Inc., Minneapolis, MN (US)

(72) Inventors: Kealan E O'Carroll, Galway (IE); Rónán Wood, Galway (IE); Colin W Meade, Westmeath (IE)

(73) Assignee: Medtronic, Inc., Minneapolis, MN (US)

( * ) Notice: Subject to any disclaimer, the term of this patent is extended or adjusted under 35 U.S.C. 154(b) by 634 days.

(21) Appl. No.: 14/812,224

(22) Filed: Jul. 29, 2015

(65) Prior Publication Data
US 2017/0028190 A1 Feb. 2, 2017

(51) Int. Cl.
*A61N 1/372* (2006.01)
*A61B 17/00* (2006.01)
(Continued)

(52) U.S. Cl.
CPC .......... *A61N 1/05* (2013.01); *A61B 17/00234* (2013.01); *A61N 1/372* (2013.01); *A61B 2017/00243* (2013.01); *A61B 2017/00305* (2013.01); *A61B 2017/00323* (2013.01); *A61B 2017/00358* (2013.01); *A61N 1/3756* (2013.01);
(Continued)

(58) Field of Classification Search
CPC ... A61N 1/05–1/06; A61M 2025/1059; A61M 25/0138; A61M 25/0141; A61M 25/0054; A61M 2025/0058; A61M 25/0067; A61M 25/0074; A61M 25/008; A61M 2025/0081; A61M 25/10–2025/1097; A61M 2025/09175; A61M 2025/09183; A61M 2025/09066; A61M 2025/09083
See application file for complete search history.

(56) References Cited

U.S. PATENT DOCUMENTS 4,710,181 A 12/1987 Fuqua
4,909,787 A 3/1990 Danforth
(Continued)

OTHER PUBLICATIONS

"Computer the size of a speck of dust created at Univeristy of Michigan" as accessed May 31, 2019; https://www.mlive.com/news/ann-arbor/2018/08/university_of_michigan_creates_5.html (published 2018).*
(Continued)

*Primary Examiner* — Wade Miles

(57) ABSTRACT

A device receptacle of a catheter resides in a sidewall thereof, which includes a proximal section, a central section extending distally from the proximal section, and a distal section extending distally from the central section. A length of the central section is approximately 30% of an overall length of the sidewall; the proximal and distal sections have approximately the same stiffness; and a stiffness of the central section, formed from a polymer material without any structural reinforcement or any other member embedded therein, is significantly less than that of the proximal and distal sections. When an operator causes the receptacle sidewall to buckle, a distal opening of a chamber of the receptacle becomes aligned with an implanted device so that the operator can bring the implanted device into the chamber to retrieve the device from the implant site.

14 Claims, 9 Drawing Sheets

(51) Int. Cl.
*A61N 1/375* (2006.01)
*A61N 1/05* (2006.01)

(52) U.S. Cl.
CPC .. *A61N 1/37205* (2013.01); *A61N 2001/0578* (2013.01)

(56) References Cited

U.S. PATENT DOCUMENTS

| | | | |
|---|---|---|---|
| 5,151,105 | A | 9/1992 | Kwan-Gett |
| 5,534,007 | A | 7/1996 | St. Germain et al. |
| 5,645,560 | A * | 7/1997 | Crocker ............ A61M 25/1002 606/108 |
| 8,615,310 | B2 | 12/2013 | Khairkhahan et al. |
| 8,706,260 | B2 | 4/2014 | Stewart et al. |
| 8,721,587 | B2 | 5/2014 | Berthiaume et al. |
| 2002/0010426 | A1 * | 1/2002 | Clayman ............... A61M 25/09 604/170.01 |
| 2004/0102719 | A1 * | 5/2004 | Keith .................... A61M 25/01 600/585 |
| 2012/0165827 | A1 | 6/2012 | Khairkhahan et al. |
| 2012/0172690 | A1 | 7/2012 | Anderson et al. |
| 2013/0103047 | A1 | 4/2013 | Steingisser et al. |
| 2014/0100521 | A1 * | 4/2014 | Mizokami ......... A61M 25/1036 604/103.09 |
| 2014/0257324 | A1 | 9/2014 | Fain |
| 2015/0039069 | A1 | 2/2015 | Rys et al. |
| 2015/0051609 | A1 | 2/2015 | Schmidt et al. |
| 2015/0094668 | A1 | 4/2015 | Wood et al. |

OTHER PUBLICATIONS (PCT/US2016/038467) PCT Notification of Transmittal of the International Search Report and the Written Opinion of the International Searching Authority, dated Sep. 19, 2016, 11 pages.

* cited by examiner

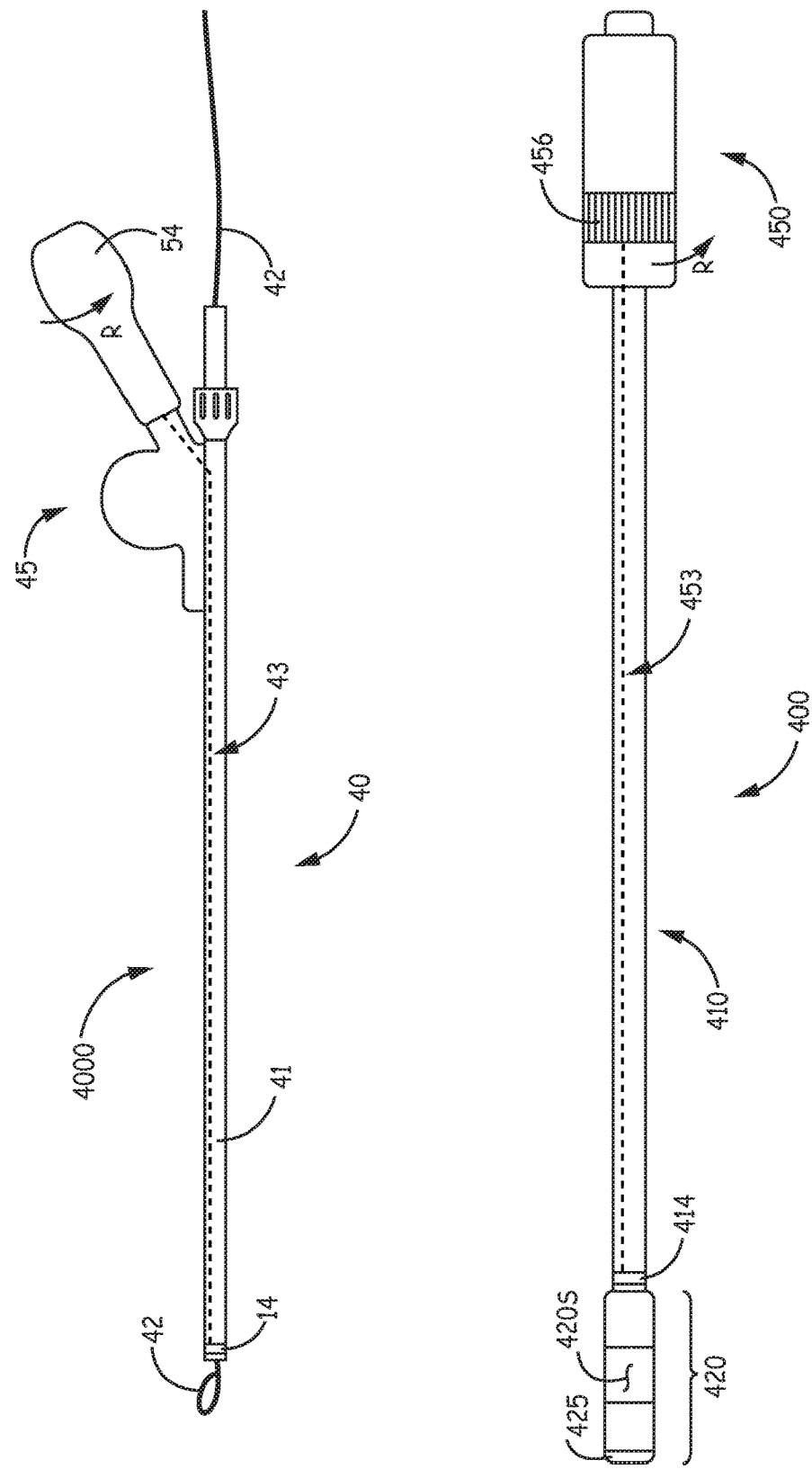

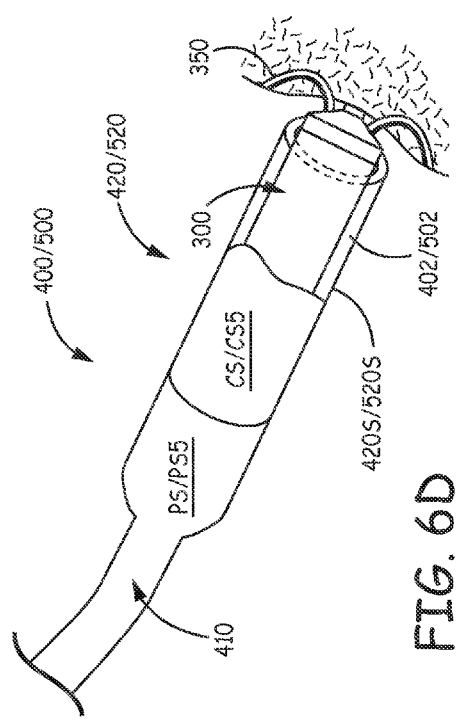
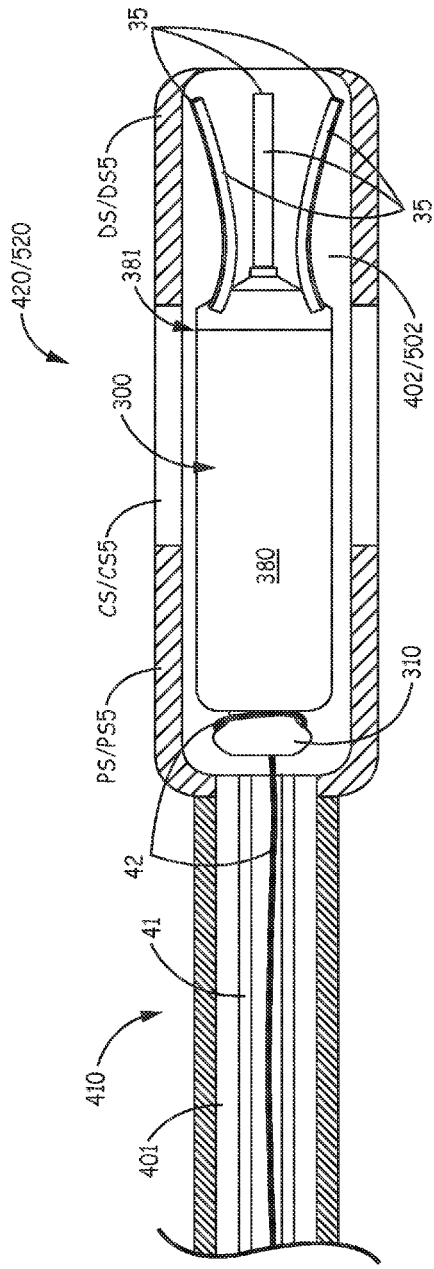

INTERVENTIONAL MEDICAL SYSTEMS, CATHETERS, AND METHODS

FIELD OF THE DISCLOSURE

The present disclosure pertains to interventional medical systems, and more particularly to systems, catheters and methods that are useful for retrieving medical devices from implant sites.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical and/or MRI compatibility issues, which are sometimes associated with elongate lead wires and well known to those skilled in the art, have motivated the development of implantable cardiac pacing devices that are wholly contained within a relatively compact package, the entirety of which is configured for implant in close proximity to the pacing site. FIG. 1 is a schematic diagram that shows potential cardiac implant sites for such a device, for example, within an appendage 102 of a right atrium RA, within a coronary vein CV (via a coronary sinus ostium CSOS), or in proximity to an apex 103 of a right ventricle RV, for example, as shown in FIG. 2.

FIG. 2 shows an implantable medical device 300 having been implanted by an operator using a catheter/tool 200, for example, like that described in the commonly assigned United States Patent Application US 2015/0094668, wherein the operator advanced tool 200 into the right heart through the inferior vena cava IVC, for example, from a femoral vein access site, and then deployed device 300 from a receptacle defined by a distal-most portion 230 of tool 200. In some cases, when it may be necessary to retrieve the implanted device, the operator can employ tool 200 to do so, but new and improved tools and methods would increase the ease and efficiency of retrieval.

SUMMARY

According to embodiments disclosed herein, a catheter includes a device receptacle joined to a distal end of an elongate shaft of the catheter, wherein the improvement to the receptacle resides in a structure of a receptacle sidewall that can be buckled to align a distal opening of a chamber of the receptacle with an implanted device thereby facilitating the retrieval of the device into the chamber. The medical device includes an electronic controller, a hermetically sealed housing containing the controller, an electrode electrically coupled to the controller and mounted in proximity to a distal end of the housing, a retrieval feature joined to a proximal end of the housing, and a fixation member mounted to the distal end of the housing, the fixation member comprising a plurality of fingers spaced apart from one another around a perimeter of the distal end of the housing, each finger being elastically deformable between a relaxed condition and an extended condition, a free end of each finger extending distally away from the distal end of the device housing, when the finger is in the extended condition. The improved receptacle sidewall of the catheter includes a proximal section extending distally from the distal end of the catheter shaft, a central section extending distally from the proximal section, and a distal section extending distally from the central section and around the distal opening of the chamber, wherein a length of the central section is approximately 30% of an overall length of the sidewall, a stiffness of the proximal section is approximately equal to a stiffness of the distal section, and a stiffness of the central section, which is formed from a polymer material without any structural reinforcement or any other member being embedded therein, is significantly less than that of the proximal and distal sections.

According to some methods, an operator employs the above-described catheter in conjunction with a retrieval tool to retrieve the medical device from an implant site, for example, by first advancing the device receptacle of the catheter to the implant site, so that a distal section of a sidewall of the receptacle is in proximity with the device retrieval feature, and then causing the central section of the device receptacle sidewall to buckle so that the a central axis of the distal opening of the chamber defined by the sidewall becomes approximately aligned with a longitudinal axis of the device at the implant site, and the proximal end of the device housing passes through the aligned distal opening. Then the operator allows the central section of the device receptacle sidewall to un-buckle, before applying a pull force along the device retrieval tool, which extends within a lumen of the catheter shaft and within the chamber of the receptacle, and which has snared the device, to bring the snared device into the chamber, so that the fingers of the device fixation member are held in the extended condition by the chamber. The operator may snare the device retrieval feature with the device retrieval tool either before or after the proximal end of the device housing passes through the aligned distal opening of the receptacle.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and:

FIG. 4A is a plan view of an interventional medical system, according to some embodiments;

FIGS. 6A-6E are schematic diagrams outlining some methods for retrieving an implanted device.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives. The term "approximately," as used in this specification and appended claims, refers to plus or minus 8% of the value given. The term "buckle" refers to an elastic deformation of a given segment of a receptacle such that the given portion is oriented along a longitudinal axis that is different from a longitudinal axis of the remaining segments of the receptacle.

Figure 3:
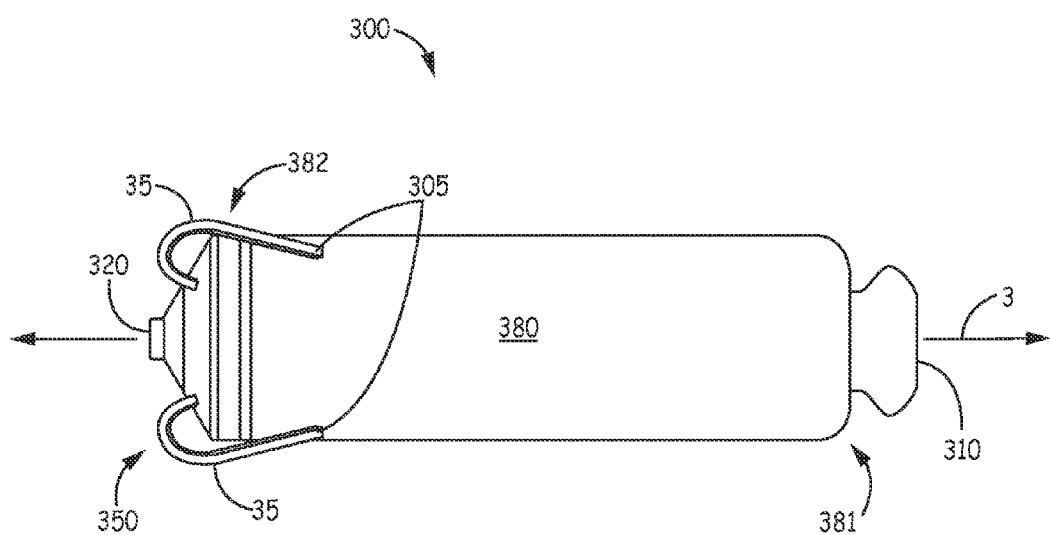
FIG. 3 is a plan view of the exemplary relatively compact implantable medical device, which may be part of an interventional medical system, according to some embodiments.

FIG. 3 is a plan view of exemplary relatively compact implantable medical device 300, which may be part of an interventional medical system, according to some embodiments. FIG. 3 illustrates device 300 including a hermetically sealed housing 380 extending from a proximal end 381 thereof to a distal end 382 thereof and along a longitudinal axis 3. Device 300 further includes an electrode 320 and a fixation member 350, both mounted in proximity to distal end 382 of housing 380, and an electronic controller (not shown), for example, a pulse generator and an associated power supply, contained in housing 380, wherein electrode 320 is electrically coupled to the controller via a hermetically sealed feedthrough assembly (not shown) such as is known in the art. Housing 380, for example, formed from a biocompatible and biostable metal such as titanium, may be overlaid with an insulative layer, for example, medical grade polyurethane, parylene, or silicone, and, although not shown, device 300 may include another electrode, for example, formed by removing a portion of the insulative layer to expose the metallic surface of housing 380. The other electrode may function in conjunction with electrode 320 for bipolar pacing and sensing, when fixation member 350 secures electrode 320 in intimate tissue contact at a target implant site. FIG. 3 further illustrates device 300 including a retrieval feature 310 joined to proximal end 381 of housing 380, wherein feature 310 is configured for snaring, for example, by a snare member 42 described below in conjunction with FIG. 4.

Figure 1:
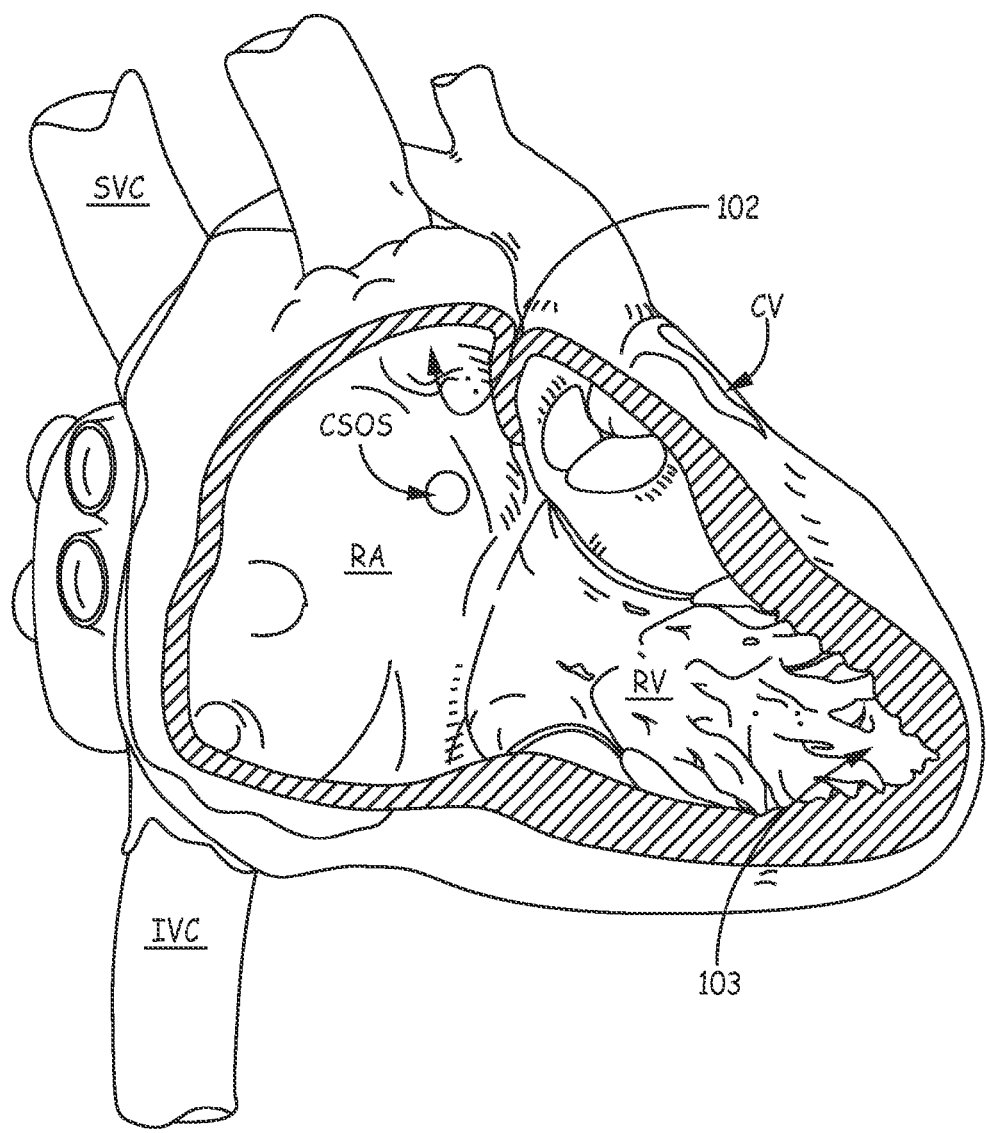
FIG. 1 is a schematic diagram showing potential implant sites for a relatively compact implantable medical device.
Figure 6A:
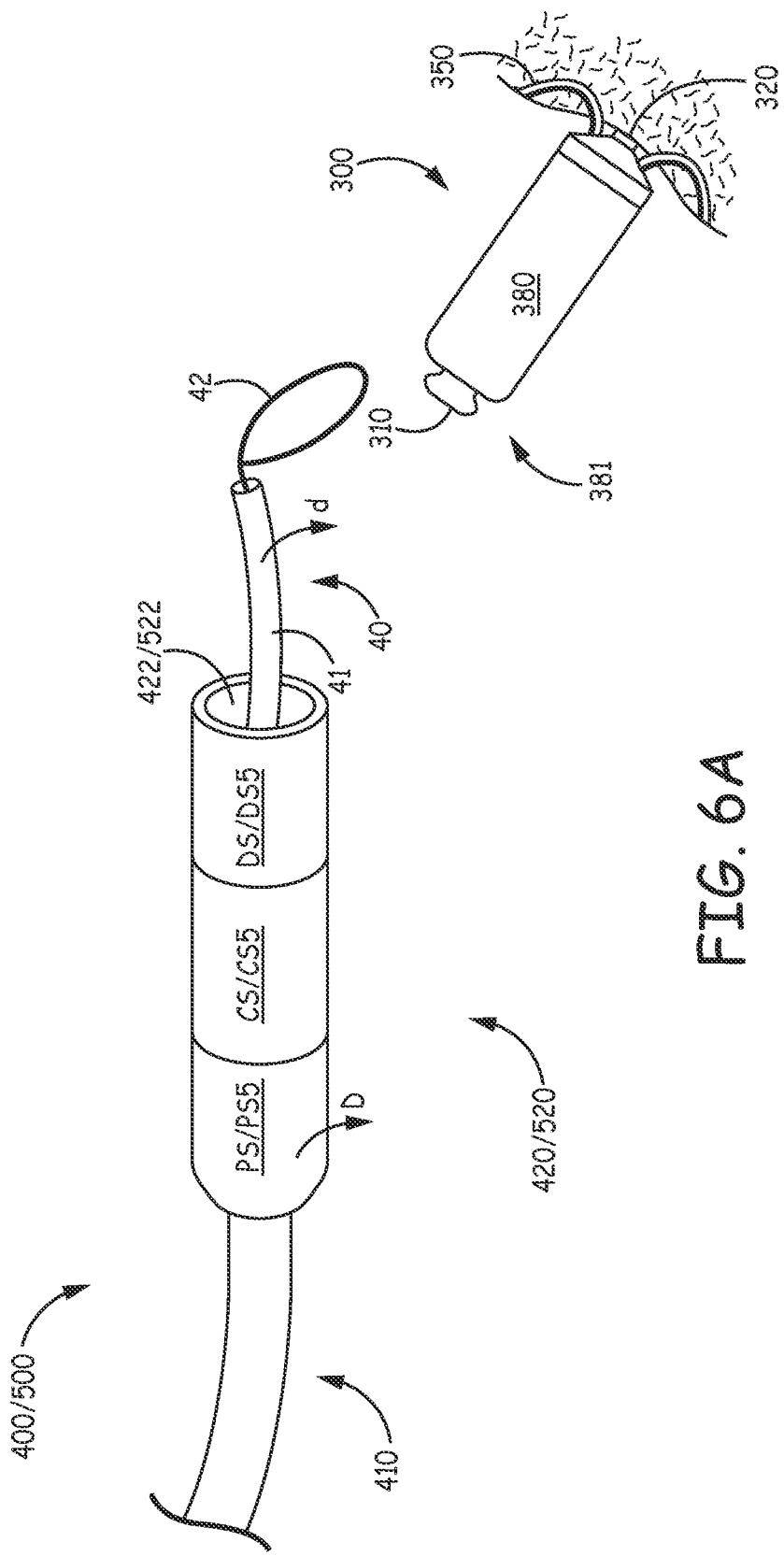

With further reference to FIG. 3, device fixation member 350 includes a plurality of fingers 35 spaced apart from one another around a perimeter of device housing distal end 382. Although only two fingers 35 of fixation member 350 are shown in FIG. 3, fixation member 350 may include as many as eight fingers 35. According to an exemplary embodiment, fixation fingers 35 are integrally formed with one another, having been cut from Nitinol tubing, according to methods known in the art. After cutting the Nitinol tubing, fingers 35 may be shaped by bending and holding fingers 35 in the illustrated curvature while heat treating, according to methods known to those skilled in the art. Fixation member 350 may be mounted to distal end 382 of device housing 380, for example, in a manner similar to that described for a fixation component 102 in co-pending and commonly assigned United States Patent Application 2012/0172690, which description is hereby incorporated by reference. The superelastic nature of Nitinol allows fingers 35 to elastically deform between a relaxed condition, which is shown, and an extended condition, in which a free end 305 of each finger extends distally away from distal end 382 of device housing 380. The extended condition of fingers 35, for example, as shown in FIG. 6E, allows for engagement of fingers 35 with tissue, for example, as shown in FIG. 6A, when device 300 is deployed at an implant site, for example, in any of the locations described above in conjunction with FIG. 1.

Figure 4B:
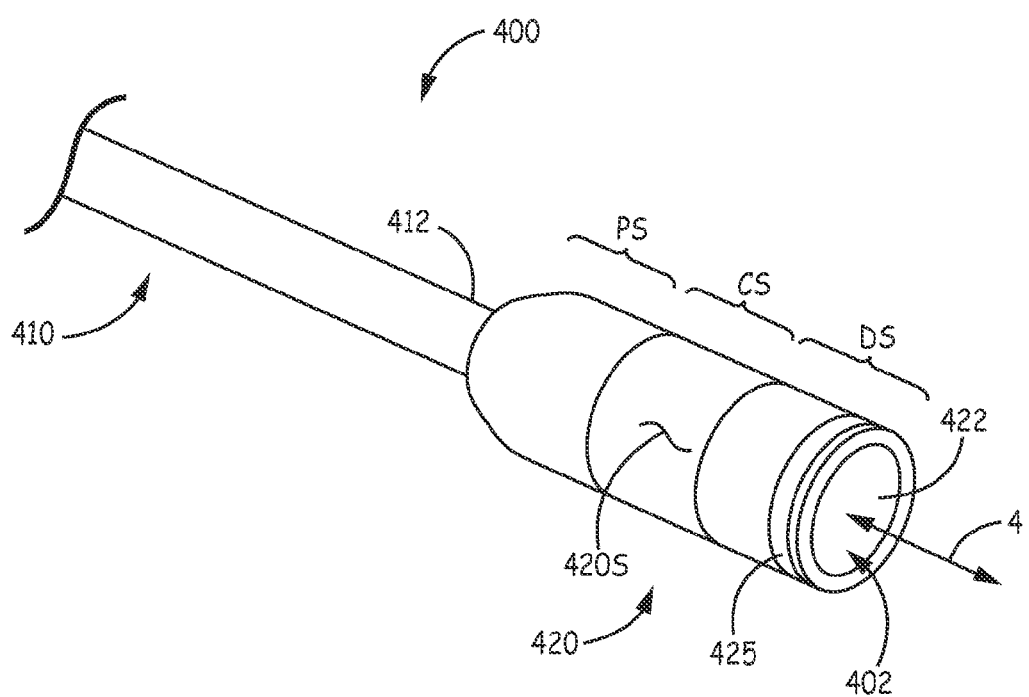
FIG. 4B is a perspective view of a portion of a catheter, according to some embodiments.

FIG. 4A is a plan view of an interventional medical system 4000, according to some embodiments. FIG. 4A illustrates system 4000 including a catheter 400 and a device retrieval tool 40. Catheter 400 includes an elongate shaft 410, which is terminated at a proximal end thereof by a handle 450, and a device receptacle 420, which is joined to a distal end 412 of shaft 410, and configured, as described below, to contain a medical device, such as device 300 of FIG. 3. Retrieval tool 40 includes an elongate shaft 41 and a snare member 42 extending within shaft 41 and being slideably engaged therewith to open and close a loop thereof. Catheter shaft 410, for example, extending over a length of approximately 100 cm, may be formed by a braid-reinforced medical grade polymer, for example, one or more appropriate grades of polyether block amide, which are arranged for decreasing stiffness from handle 450 to shaft distal end 412 (e.g., PEBAX® 3533, 6333, 4033, and 7233) and are reinforced with a stainless steel braid. Although not shown, shaft 410 may include a pre-formed curvature in proximity to distal end 412. Catheter shaft 410 includes a lumen 401, seen in FIGS. 5B and 6E, that is in fluid communication with a chamber 402 defined by a sidewall 420S of device receptacle 420, seen in FIG. 4B and FIG. 6E, so that an operator may pass retrieval tool 40 through lumen 401 and chamber 402 to retrieve a medical device, for example, device 300, from an implant site, as will be described in greater detail below. Lumen 401 may have a diameter of approximately 0.154 inch (3.9 mm), and chamber 402 may have a diameter of approximately 0.278 inch (7 mm). It should be noted that catheter 400 may also be employed to deliver device 300 to the implant site.

According to some preferred embodiments, catheter 400 and retrieval tool 40 each include a deflection wire assembly, and FIG. 4A shows a deflection wire band 414, 14 of each assembly mounted to the corresponding shaft 410, 41, and actuators 456, 54 of each assembly integrated into respective handles 450, 45. Those skilled in the art will understand that each deflection wire assembly includes an elongate deflection wire 453, 43 extending along a length of the corresponding shaft 410, 41 and being coupled, at a distal end thereof, to the corresponding band 414, 14, and at a proximal end thereof, to the corresponding actuator 456, 54, each of which may be rotated per arrow R to deflect the corresponding shaft 410, 41.

FIG. 4B is an enlarged perspective view of a distal portion of catheter 400, according to some embodiments, wherein a structure of receptacle sidewall 420S is delineated. FIG. 4B illustrates sidewall 420S defining the aforementioned chamber 402 of device receptacle 420, configured to contain medical device 300, wherein sidewall 420S includes a proximal section CS, a central section CS, and a distal section DS. According to the illustrated embodiment, proximal section PS, which extends distally from distal end 412 of catheter shaft 410, and distal section DS, which extends distally from central section CS, have approximately the same stiffness, for example being formed from a polymer material that has a durometer of approximately 72 on a Shore D scale, whereas a stiffness of central section CS, which extends from proximal section PS to distal section DS, is significantly less than that of proximal and distal sections PS, DS, for example, being formed from a polymer material having a relatively lower durometer, such as approximately 55 on a Shore D scale, to promote a buckling of sidewall 420S that, according methods described below in conjunction with FIGS. 6A-E, generally aligns a central axis 4 of a distal opening 422 of chamber 402 with longitudinal axis 3 of device 300 at an implant site. An overall length of receptacle 420 may be approximately 35 mm, wherein a length of central section CS is preferably approximately 30% of the overall length, or approximately 10 mm. Shorter lengths of central section CS were found to be somewhat more difficult to buckle and/or did not align central axis 4 with longitudinal axis 3 as well for most commonly encountered relative orientations of catheter receptacle 420 and implanted device 300. According to an exemplary embodiment, proximal and distal sections PS, DS are formed from PEBAX® 7233, and central section CS is formed from PEBAX® 5533, without any structural reinforcement or any other member embedded therein.

With further reference to FIG. 4B, a distal opening 422 of chamber 402, around which receptacle sidewall distal section DS extends, is sized to receive passage of medical device 300 therethrough, for example, in retrieving device 300 from an implant site, and chamber 402 is sized to hold fixation fingers 35 of the contained device 300 in the extended condition (FIG. 6E). FIGS. 4A-B further illustrate receptacle 420 of catheter 400 including a radiopaque marker band 425, which is preferably mounted to receptacle sidewall distal section DS. According to an exemplary embodiment, marker band 425 is formed from a polyamide material with a radiopaque filler, for example, Tungsten-filled Vestamid®, that is bonded to distal section DS.

Figure 5A:
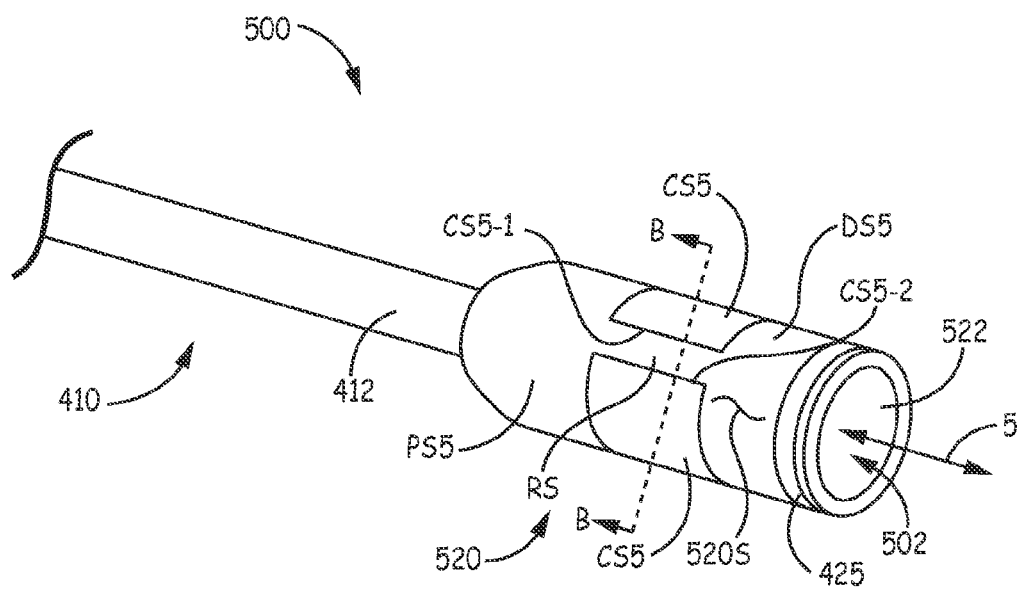
FIG. 5A is a perspective view of a portion of a catheter, according to some alternate embodiments.
Figure 5B:
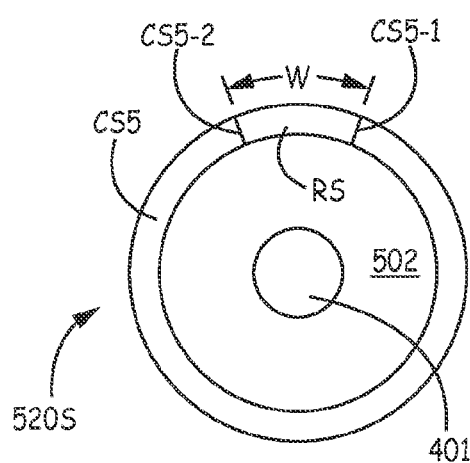
FIG. 5B is an axial cross-section through section line B-B of FIG. 5A.

FIG. 5A is a perspective view of a portion of a catheter 500, according to some alternate embodiments; and FIG. 5B is an axial cross-section through section line B-B of FIG. 5A. Catheter 500, like catheter 400, includes elongate shaft 410, but FIG. 5A illustrates a receptacle 520 of catheter 500, which is joined to distal end 412 of shaft 410, including a sidewall 520S that differs from receptacle sidewall 420S in that a central section CS5 thereof, which extends from a proximal section PS5 of sidewall 520S to a distal section DS5 of sidewall 520S, includes first and second longitudinally extending edges CS5-1, CS5-2. With reference to FIGS. 5A-B, receptacle sidewall central section CS5 extends in a C-shape, from first edge CS5-1 to second edge CS5-2, and sidewall 520S further includes a rib section RS that extends circumferentially between edges CS5-1, CS5-2, for example, having a width w of approximately 2.5 mm, and that extends longitudinally from proximal section PS5 to distal section DS5. According to the illustrated embodiment, rib section RS, proximal section PS5, and distal section DS5 all have approximately the same stiffness, while a stiffness of central section CS5 is significantly less. According to some exemplary embodiments, each of proximal, distal and rib sections PS5, DS5, RS is formed from a polymer material that has a durometer of approximately 72 on a Shore D scale, and central section CS5, from a polymer material that has a durometer of approximately 55 on a Shore D scale. In some embodiments, proximal, distal and rib sections PS5, DS5, RS are integrally formed, for example, from PEBAX® 7233, and central section CS5 is formed from PEBAX® 5533, without any structural reinforcement or any other member embedded therein.

A chamber 502 defined by sidewall 520S, and a distal opening 522 thereof are sized similarly to those defined by sidewall 420S, to contain and allow passage of device 300 therethrough. Like sidewall 420S of receptacle 420, the structure of sidewall 520S promotes a buckling thereof, according to methods described below in conjunction with FIGS. 6A-E, to generally align a central axis 5 of distal opening 522 with longitudinal axis 3 of device 300 at the implant site. But rib section RS of sidewall 520S promotes unidirectional buckling, and enhances a columnar strength of sidewall 520S to better hold fixation fingers 35 of the contained device 300 in the extended condition (FIG. 6E). Like receptacle 420 of catheter 400, an overall length of receptacle 520 from the junction of sidewall proximal section PS5 with shaft 410 to distal opening 522 of chamber 502 is approximately 35 mm, and a length of central section CS5 is approximately 30% of the overall length, or approximately 10 mm. With further reference to FIG. 5A, receptacle also includes radiopaque marker band 425, for example, bonded to distal section DS5.

Means for manufacturing each of catheters 400, 500 may involve reflowing adjacent polymer materials into one another to form junctions therebetween, for example, by positioning individual sections on a mandrel that has a low friction coating, and then placing a heat shrinking polymer tube thereabout, followed by heating the sections to a temperature that exceeds a melting temperature of each material so that the materials of adjacent sections flow into one another to form junctions therebetween. A hydrostatic inward pressure exerted by the overlaid heat shrinking polymer tubing during the reflow process ensures smooth transitions between sections and an overall smooth surface finish. Alternative manufacturing methods may employ on/off type extrusion using the various polymer materials at the time of extrusion, or the individual sections could be adhesive bonded to one another and/or chemically dissolved into one another.

Figure 2:
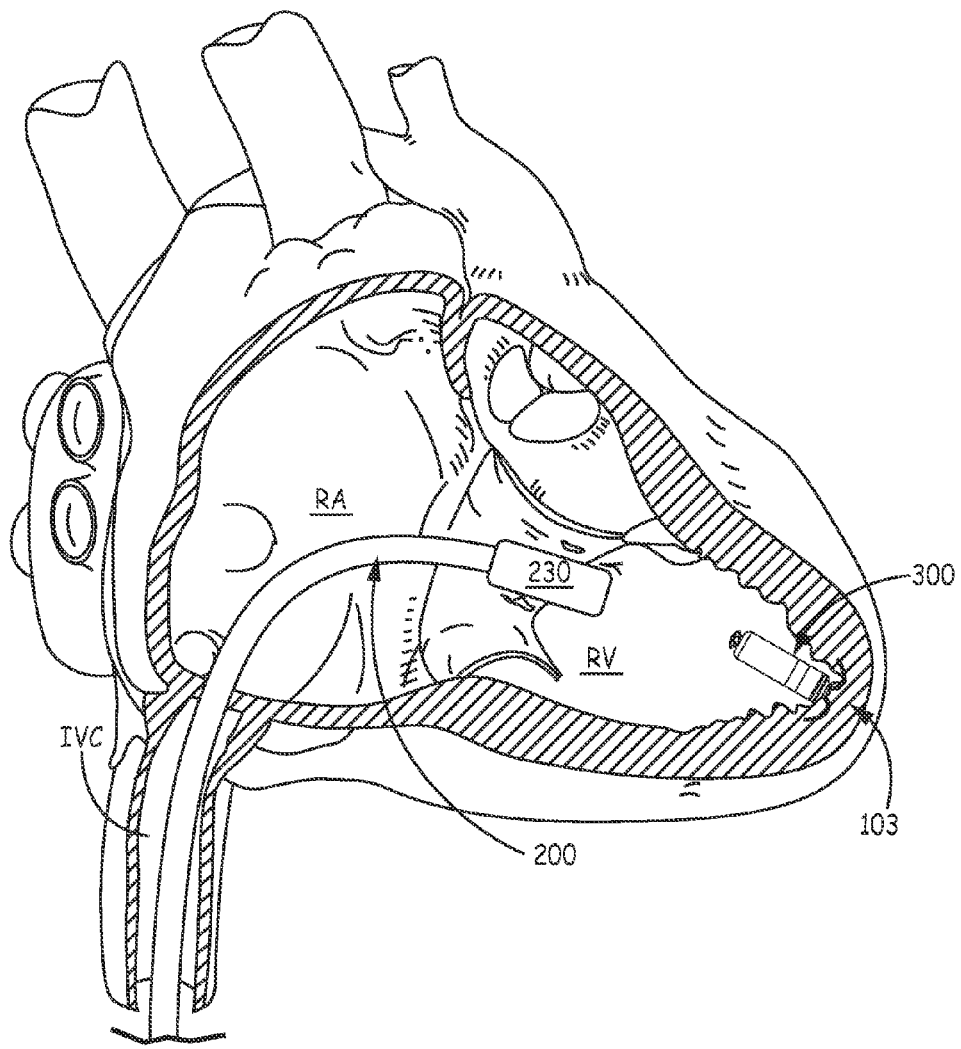
FIG. 2 is a schematic diagram showing an exemplary relatively compact implantable medical device having been delivered from a catheter to an implant site.
Figure 6C:
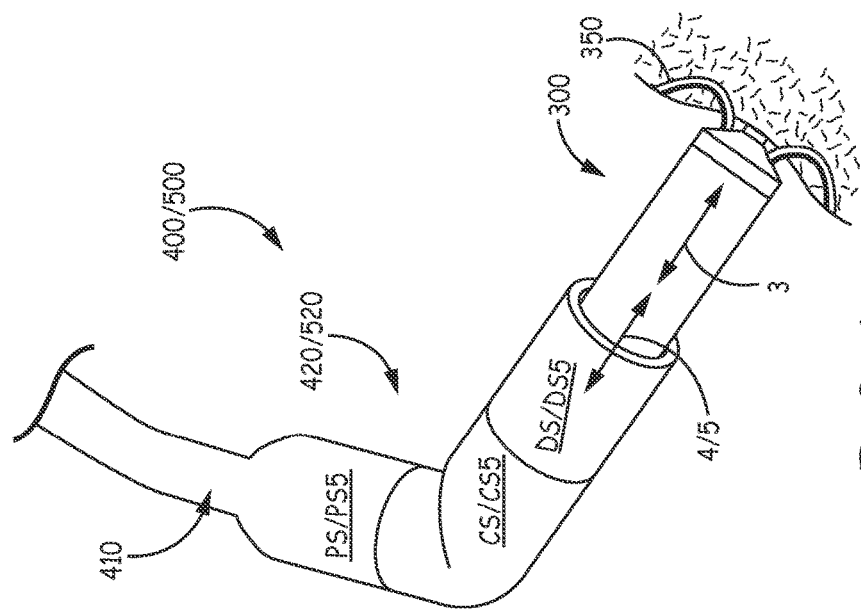
Figure 6B:
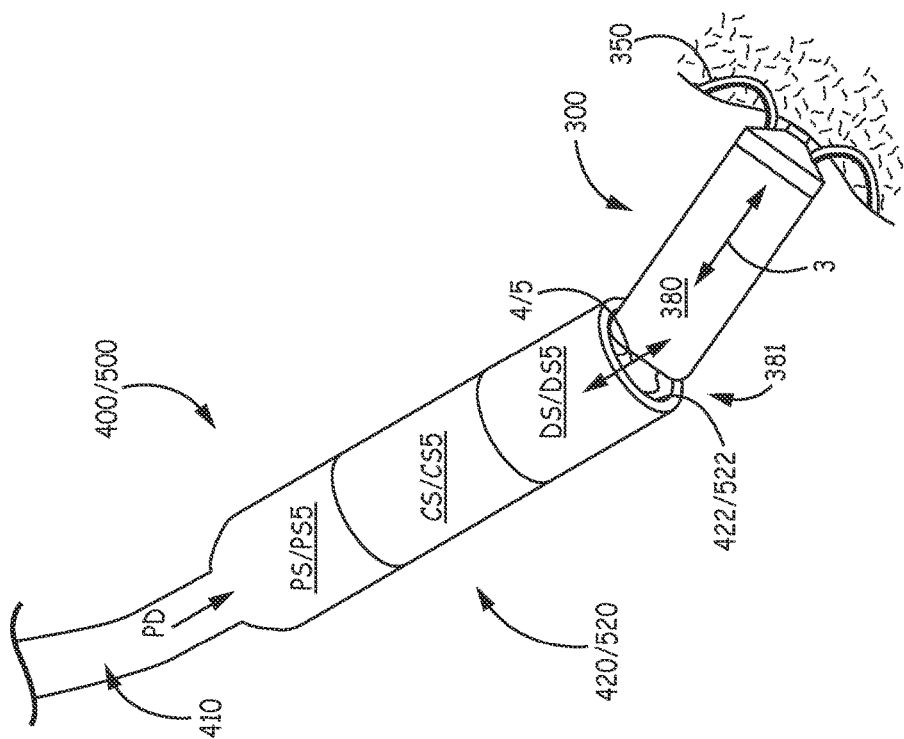

FIGS. 6A-6E are schematic diagrams outlining some methods for retrieving device 300 from an implant site, for example, from any of the sites described above in conjunction with FIG. 1, and with either of catheters 400, 500. FIG. 6A illustrates device receptacle 420/520 of catheter 400/500 having been advanced to an implant site, for example, through a 23 F introducer sheath that provides vascular access at a femoral vein puncture site. With reference back to FIG. 2, if device 300 is implanted in the apex 103 of the right ventricle RV, catheter 400/500, having been introduced through the femoral vein, may be positioned similarly to the illustrated catheter 200 for retrieval of device 300. FIG. 6A further illustrates device retrieval tool 40 having been passed out through distal opening 422, 522 of receptacle 420/520 with snare member 42 deployed to snare device retrieval feature 310, according to some methods, wherein the operator may deflect, per arrow d, retrieval tool shaft 41 via the above-described deflection wire assembly thereof to maneuver the deployed snare member 42 into position around retrieval feature 310. Then, once retrieval feature 310 is snared, the operator may advance catheter 400/500 over retrieval tool 40 until receptacle distal section DS/DS5 is brought into contact with device proximal end 381, as shown in FIG. 6B. Alternately, the operator may bring distal section DS/DS5 into contact with device proximal end 381 without passing device retrieval tool 40 out through distal opening 422/522 and prior to snaring device retrieval feature 310, in which case, retrieval feature 310 may be snared by snare member 42 within receptacle 420/520. In either case, according to some methods, the operator may actuate the above-described deflection wire assembly of catheter 400/500 to deflect shaft 410, per arrow D, in maneuvering receptacle 420/520 into the position shown in FIG. 6B.

FIG. 6B illustrates a relatively severe misalignment of central axis 4/5 of receptacle distal opening 422/522 with longitudinal axis 3 of the implanted device 300, which is corrected by causing receptacle central section CS/CS5 to buckle, for example, by applying a push force along catheter 400/500, per arrow PD, when receptacle sidewall distal section DS/DS5 is in contact with device proximal end 381. The push force may be accompanied by applying a pull force along retrieval tool 40, after snaring device retrieval feature 310. FIG. 6C shows the buckled central section CS/CS5 that brings central axis 4/5 into alignment with longitudinal axis 3 of the implanted device 300 so that device proximal end 381 passes through the approximately aligned distal opening 422/522. Then the operator may release the push force along catheter 400/500 so that section CS/CS5 can un-buckle, as shown in FIG. 6D, before applying a pull force along retrieval tool 40 that brings the snared device 300 into the chamber so that fingers 35 of device fixation member 350 are held in the extended condition by chamber 402/502, with each free end 305 thereof extending distally away from distal end 382 of device housing 380 for example, as shown in FIG. 6E.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

For example, the following Items are illustrative of further embodiments:

Item 1. An interventional medical system comprising an implantable medical device, a device retrieval tool, and a catheter; the medical device comprising an electronic controller, a hermetically sealed housing containing the controller, an electrode electrically coupled to the controller and mounted in proximity to a distal end of the housing, an attachment feature joined to a proximal end of the housing, and a fixation member mounted to the distal end of the housing, the fixation member comprising a plurality of fingers spaced apart from one another around a perimeter of the distal end of the housing, each finger being elastically deformable between a relaxed condition and an extended condition, a free end of each finger extending distally away from the distal end of the device housing, when the finger is in the extended condition; the device retrieval tool configured to snare the attachment feature of the medical device; and the catheter comprising an elongate shaft and a device receptacle joined to a distal end of the shaft, the shaft including a longitudinally extending lumen configured to receive passage of the device retrieval tool therethrough, the device receptacle including a chamber in fluid communication with the shaft lumen, the chamber being sized to hold the fingers of the device fixation member in the extended condition when the medical device is contained within the chamber, and the chamber having a distal opening sized to receive passage of the device therethrough; and wherein an improvement to the device receptacle of the catheter comprises:

a sidewall, which defines the chamber, comprising a proximal section extending distally from the distal end of the catheter shaft, a central section extending distally from the proximal section, and a distal section extending distally from the central section and around the distal opening of the chamber, a length of the central section being approximately 30% of an overall length of the sidewall, a stiffness of the proximal section being approximately equal to a stiffness of the distal section, and a stiffness of the central section being significantly less than that of the proximal and distal sections; and wherein the central section of the sidewall comprises a polymer material without any structural reinforcement or any other member being embedded therein.

Item 2. The system of item 1, wherein:

the central section of the device receptacle sidewall of the catheter includes a first longitudinally extending edge and a second longitudinally extending edge, the first and second edges extending along the length of the central section, and the central section extending circumferentially from the first edge to the second edge in a C-shape; and the device receptacle sidewall of the catheter further comprises a rib section extending between the first and second edges of the central section and longitudinally from the proximal section to the distal section, a stiffness of the rib section being approximately equal to that of the proximal and distal sections.

Item 3. The system of any one of items 1-2, wherein the proximal, rib, and distal sections of the device receptacle sidewall are integrally formed.

Item 4. The system of any one of items 1-2, wherein an outer diameter of the device receptacle sidewall is between approximately 7.5 mm and approximately 8 mm, and a width of the rib section of the sidewall, from the first edge to the second edge of the central section of the sidewall, is approximately 2.5 mm.

Item 5. The system of any one of items 1-4, wherein:

the proximal and distal sections of the device receptacle sidewall of the catheter comprise a polymer material having a durometer of approximately 72 on a Shore D scale; and the polymer material comprising the central section of the device receptacle sidewall has a durometer of approximately 55 on a Shore D scale.

Item 6. The system of any one of items 1-5, wherein the catheter shaft further includes a deflection wire assembly, the deflection wire assembly including a deflection wire and a deflection band, the deflection wire extending along a length of the shaft, the deflection band being mounted around the sidewall of the shaft and coupled to a distal end of the deflection wire.

Item 7. A catheter comprising an elongate shaft and a receptacle joined to a distal end of the shaft, the receptacle including a chamber configured to contain an implantable medical device therein, the medical device comprising an electronic controller, a hermetically sealed housing containing the controller, an electrode electrically coupled to the controller and mounted in proximity to a distal end of the housing, an attachment feature joined to a proximal end of the housing, and a fixation member mounted to the distal end of the housing, the fixation member comprising a plurality of fingers spaced apart from one another around a perimeter of the distal end of the housing, each finger being elastically deformable between a relaxed condition and an extended condition, a free end of each finger extending distally away from the distal end of the device housing, when the finger is in the extended condition, the chamber being sized to hold the fingers of the device fixation member in the extended condition when the medical device is contained within the chamber, and the chamber having a distal opening sized to receive passage of the device therethrough; and wherein an improvement to the receptacle comprises:

a sidewall, which defines the chamber, comprising a proximal section extending distally from the distal end of the catheter shaft, a central section extending distally from the proximal section, and a distal section extending distally from the central section and around the distal opening of the chamber, a length of the central section being approximately 30% of an overall length of the sidewall, a stiffness of the proximal section being approximately equal to a stiffness of the distal section, and a stiffness of the central section being significantly less than that of the proximal and distal sections; and wherein the central section of the sidewall comprises a polymer material without any structural reinforcement or any other member being embedded therein.

Item 8. The catheter of item 7, wherein:
the central section of the receptacle sidewall includes a first longitudinally extending edge and a second longitudinally extending edge, the first and second edges extending along the length of the central section, and the central section extending circumferentially from the first edge to the second edge in a C-shape; and the receptacle sidewall of the catheter further comprises a rib section extending between the first and second edges of the central section and longitudinally from the proximal section to the distal section, a stiffness of the rib section being approximately equal to that of the proximal and distal sections.

Item 9. The catheter of any one of items 7-8, wherein the proximal, rib, and distal sections of the receptacle sidewall are integrally formed.

Item 10. The catheter of any one of items 7-8, wherein an outer diameter of the receptacle sidewall is between approximately 7.5 mm and approximately 8 mm, and a width of the rib section of the sidewall, from the first edge to the second edge of the central section of the sidewall, is approximately 2.5 mm.

Item 11. The catheter of any one of items 7-10, wherein:
the proximal and distal sections of the receptacle sidewall comprise a polymer material having a durometer of approximately 72 on a Shore D scale; and the polymer material comprising the central section of the receptacle sidewall has a durometer of approximately 55 on a Shore D scale.

Item 12. The catheter of any one of items 7-11, wherein the shaft includes a deflection wire assembly, the deflection wire assembly including a deflection wire and a deflection band, the deflection wire extending along a length of the shaft, the deflection band being mounted around the sidewall of the shaft in proximity to the receptacle and being coupled to a distal end of the deflection wire.

Thus, various examples of interventional medical systems have been described. It is recognized that various modifications may be made to the described embodiments without departing from the scope of the following claims.

We claim:

1. An interventional medical system, comprising:
an implantable medical device comprising a hermetically sealed housing containing an electronic controller, an electrode coupled to the housing, a retrieval feature coupled to a proximal end of the housing, and a fixation member coupled to the distal end of the housing;
a device retrieval tool configured to snare the retrieval feature of the medical device; and
a catheter comprising an elongate shaft and a device receptacle coupled to a distal end of the shaft, the shaft including a longitudinally extending lumen configured to receive the device retrieval tool therethrough, the device receptacle including a chamber in fluid communication with the lumen, the chamber being sized to hold the fixation member of the device, and the chamber having a distal opening sized to receive passage of the device therethrough, and wherein the device receptacle of the catheter comprises:
a sidewall, which defines the chamber, comprising a proximal section extending distally from the distal end of the catheter shaft, a central section extending distally from the proximal section, and a distal section extending distally from the central section and around the distal opening of the chamber, a length of the central section being approximately 30% of an overall length of the sidewall, a stiffness of the proximal section being approximately equal to a stiffness of the distal section, and a stiffness of the central section being significantly less than that of the proximal and distal sections; and
wherein the central section of the sidewall comprises a polymer material without any structural reinforcement or any other member being embedded therein.

2. The system of claim 1, wherein:
the central section of the device receptacle sidewall of the catheter includes a first longitudinally extending edge and a second longitudinally extending edge, the first and second edges extending along the length of the central section, and the central section extending circumferentially from the first edge to the second edge in a C-shape; and
the device receptacle sidewall of the catheter further comprises a rib section extending between the first and second edges of the central section and longitudinally from the proximal section to the distal section, a stiffness of the rib section being approximately equal to that of the proximal and distal sections.

3. The system of claim 2, wherein the proximal, rib, and distal sections of the device receptacle sidewall are integrally formed.

4. The system of claim 2, wherein an outer diameter of the device receptacle sidewall is between approximately 7.5 mm and approximately 8 mm, and a width of the rib section of the sidewall, from the first edge to the second edge of the central section of the sidewall, is approximately 2.5 mm.

5. The system of claim 1, wherein the fixation member includes a segment that is elastically deformable between a relaxed condition and an extended condition and wherein the chamber is sized to hold the fixation member in the extended condition when the medical device is contained within the chamber.

6. The system of claim 1, wherein:
the proximal and distal sections of the device receptacle sidewall of the catheter comprise a polymer material having a durometer of approximately 72 on a Shore D scale; and
the polymer material comprising the central section of the device receptacle sidewall has a durometer of approximately 55 on a Shore D scale.

7. The system of claim 1, wherein the catheter shaft further includes a deflection wire assembly, the deflection wire assembly including a deflection wire and a deflection band, the deflection wire extending along a length of the shaft, the deflection band being mounted around a sidewall of the shaft and coupled to a distal end of the deflection wire.

8. A retrieval catheter, comprising:
an elongate shaft having an elongate shaft distal end; and
a receptacle having a receptacle proximal end being coupled to the elongate shaft distal end and a receptacle distal end that includes a receptacle opening, wherein the receptacle comprises:
a sidewall comprising:
a proximal section extending distally from the distal end of the catheter shaft;
a central section defining a first longitudinally extending edge and a second longitudinally extending edge, each edge extending along a length of the central section, the central section extending distally from the proximal section and circumferentially from the first edge to the second edge in a C-shape;

a distal section extending distally from the central section; and a rib section extending between the first and second edges of the central section and longitudinally from the proximal section to the distal section, a stiffness of the rib section being approximately equal to that of the proximal and distal sections, wherein the sidewall defines a chamber configured to receive, via the receptacle opening, and contain an implantable medical device comprising a hermetically sealed housing containing an electronic controller, an electrode coupled to the housing, a retrieval feature coupled to a proximal end of the housing, and a fixation member coupled to the distal end of the housing, wherein the distal section of the sidewall extends around a distal opening of the chamber, wherein the length of the central section is approximately 30% of an overall length of the sidewall, wherein a stiffness of the proximal section is approximately equal to a stiffness of the distal section, wherein a stiffness of the central section is significantly less than that of the proximal and distal sections, and wherein the central section of the sidewall comprises a polymer material without any structural reinforcement or any other member being embedded therein.

9. The catheter of claim 8, wherein the proximal, rib, and distal sections of the receptacle sidewall are integrally formed.

10. The catheter of claim 8, wherein an outer diameter of the receptacle sidewall is between approximately 7.5 mm and approximately 8 mm, and a width of the rib section of the sidewall, from the first edge to the second edge of the central section of the sidewall, is approximately 2.5 mm.

11. The catheter of claim 8, wherein:

the proximal and distal sections of the receptacle sidewall comprise a polymer material having a durometer of approximately 72 on a Shore D hardness scale; and the polymer material comprising the central section of the receptacle sidewall has a durometer of approximately 55 on a Shore D hardness scale.

12. The catheter of claim 8, wherein the shaft includes a deflection wire assembly, the deflection wire assembly including a deflection wire and a deflection band, the deflection wire extending along a length of the shaft, the deflection band being mounted around a sidewall of the shaft in proximity to the receptacle and being coupled to a distal end of the deflection wire.

13. The catheter of claim 8, wherein the fixation member includes a segment that is elastically deformable between a relaxed condition and an extended condition and wherein the chamber is sized to hold the fixation member in the extended condition when the medical device is contained within the chamber.

14. The catheter of claim 8, further comprising a snare, the snare comprising a loop configured to retrieve the implantable medical device, wherein the elongate shaft includes a longitudinally extending lumen configured to receive the snare therethrough the catheter.

* * * * *